United States Patent [19]

Kugimiya

[11] Patent Number: 4,547,073
[45] Date of Patent: Oct. 15, 1985

[54] SURFACE EXAMINING APPARATUS AND METHOD

[75] Inventor: Koichi Kugimiya, Toyonaka, Japan

[73] Assignee: Matsushita Electric Industrial Co., Ltd., Kadoma, Japan

[21] Appl. No.: 348,086

[22] Filed: Feb. 11, 1982

[30] Foreign Application Priority Data

Feb. 17, 1981 [JP] Japan .............................. 56-21775[U]
May 13, 1981 [JP] Japan .................................. 56-71719

[51] Int. Cl.⁴ ...................... G01B 11/30; G01N 21/88
[52] U.S. Cl. .................................... 356/371; 356/445; 356/237
[58] Field of Search ............... 356/445, 237, 371, 430, 356/446; 250/550, 562, 563, 572

[56] References Cited

U.S. PATENT DOCUMENTS

| | | | |
|---|---|---|---|
| 3,176,306 | 3/1965 | Burns | 356/237 |
| 3,815,998 | 6/1974 | Tietze | 356/237 X |
| 3,964,830 | 6/1976 | Ikeda et al. | 356/237 X |
| 4,215,939 | 8/1980 | Miller et al. | 356/371 |
| 4,290,698 | 9/1981 | Milana | 356/371 |
| 4,330,205 | 5/1982 | Murakami et al. | 356/237 |

FOREIGN PATENT DOCUMENTS 0157841 12/1981 Japan ................................. 356/237

Primary Examiner—Vincent P. McGraw
Assistant Examiner—S. A. Turner
Attorney, Agent, or Firm—Cushman, Darby & Cushman

[57] ABSTRACT

The surface of a polished semiconductor wafer is examined by an apparatus comprising a light source, a first optical means for converging the light to a parallel light and projecting it onto the surface to be examined and a second optical means for converging the light reflected by the surface and projecting it onto a light receiving screen. If the surface has a defect, such as a crystal imperfection, the surface forms a very slight recess or wave, for example, having a sub-micron depth and having an opening diameter of several mm. When such surface is examined by the above-mentioned apparatus, specific shading patterns, lines, stripes or dots are projected on the light-receiving screen, thereby making detection of wafer defects easy and even subject to automation.

26 Claims, 17 Drawing Figures

SURFACE EXAMINING APPARATUS AND METHOD

BACKGROUND OF THE INVENTION

1. Technical Field of the Invention

The present invention relates to an apparatus and method for non-contact examination of a mirror-flat surface.

2. Description of the Prior Art

For examination of a mirror-like polished flat surface, various methods have been proposed. For example, one method is that a very narrow (several ten microns) laser light beam is projected on the mirror-flat surface and the reflected light is examined by an image sensor whereby variation of angle of the reflecting surface is calculated from the shifting of the beam incident on the image sensor, and the same measuring processes are repeated by displacing or scanning the object matter a number of times. This method can detect such shallow uneveness of up to 0.5 μm, but the problem is that the detectable limit is 0.5 μm and a flat large recess or a groove or a stain lying in the direction of the displacement can not be detected, the apparatus is expensive and the operation requires high skill.

Another conventional method is enlarging a narrow laser beam to enlarged parallel rays and projecting these rays on the surface, and superposing the reflected rays over the original rays and projecting them on a receiving screen, thereby forming an interference stripe pattern, and detecting unevenness of the mirror-flat surface. This method is useful in observing the surface at a glance with ease and therefore detection of scratches or the like can be easily made. However, this method has difficulty in detecting slight recesses such as of 0.5 μm or shallower, moderate recess having a size of 3 to 10 mm. or stains. Also, the adjustment of the apparatus requires skilled workers and the apparatus is expensive.

In recent years, especially in the semiconductor industry, quality requirements for silicon substrate has become more and more strict as the integration density of the semiconductor devices progress higher and higher. Since internal stress of the semiconductor substrate is likely to induce defect on the mirror-polished surface thereof, the surface perfection is regarded as an important item in checking the substrate. However, in general, the surface examination is made by a skilled worker by a simple observation with his naked eyes by reflecting oblique rays or reflecting straight light source on the surface, and such examination depends much on the skill and condition of workers.

Figure 1:
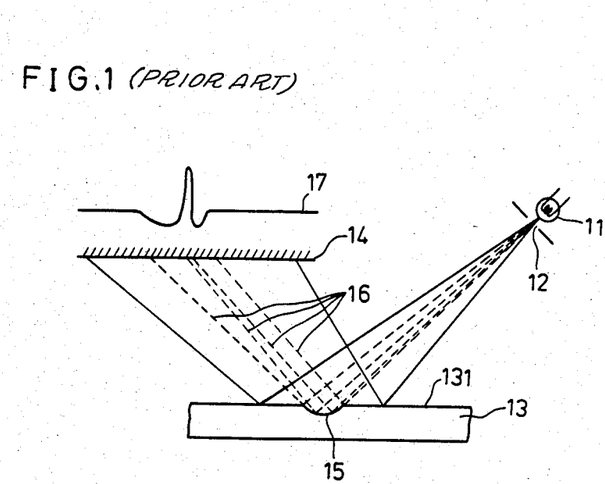
FIG. 1 is a schematical sectional elevation view showing the principle of a conventional primitive surface examining method in accordance with the mysterious mirror method.

In Japan and China, mysterious mirror divine has been known which uses a simple metal-made mirror of very old tradition but having a hidden very slight intangible surface unevenness, and when sun-light or moon-light is reflected by these mirrors and projected on a far-away screen in a dark room, a mysterious pattern or character appears under a specified condition, mainly the specific distance from the mirror to the screen. The inventor tried to utilize the way of projecting the reflected light to a far-away screen for examining specific patterns corresponding to such very shallow and moderate recesses or defects on the surface. FIG. 1 schematically shows the apparatus of the above-mentioned examination after "mysterious mirror divine", where a light beam from a small light source 11 is projected through a pin hole 12 onto the mirror-polished silicon substrate 13 where a shallow and wide recess 15 exists. If there is no recess or protrusion or stain on the surface, then evenly distributed rays are reflected on the screen 14 thereby forming a simple even-brightness image of the corresponding shape to the mirror surface 131. However, since the shallow and moderate recess 15 exists on the surface 131, the recess part converges light as a concave mirror, and reflects rays as shown by the dotted lines 16. Therefore, the light image formed on the screen 14 has non-uniform distribution of brightness as shown by a curve 17. That is, in general the light image on the screen has a bright spot or bright region when the mirror face has a concave defect, and a dark spot or dark area when the mirror face has a convex defect. When the surface has parallel recess-shaped unevenness, the light image becomes a parallel shadow pattern, and one can detect such a shallow recess of 0.3 μm depth and 1 to 3 mm size, but distance from the sample substrate 13 and the screen 14, as well as the distance from the light source 11 and the sample substrate 13 needs to be a large value such as 3–6 m when considering the defect recess 15 of a concave mirror of a focal length of several ten meters. Such a large apparatus is not practical for actual use in a factory. Furthermore, such a long distance induces other problems such as poor illuminance of the screen image, necessitating a large dark-room or a high power point light source, and lowering of resolution of detection due to flaring or trembling of the image, etc.

Figure 2:
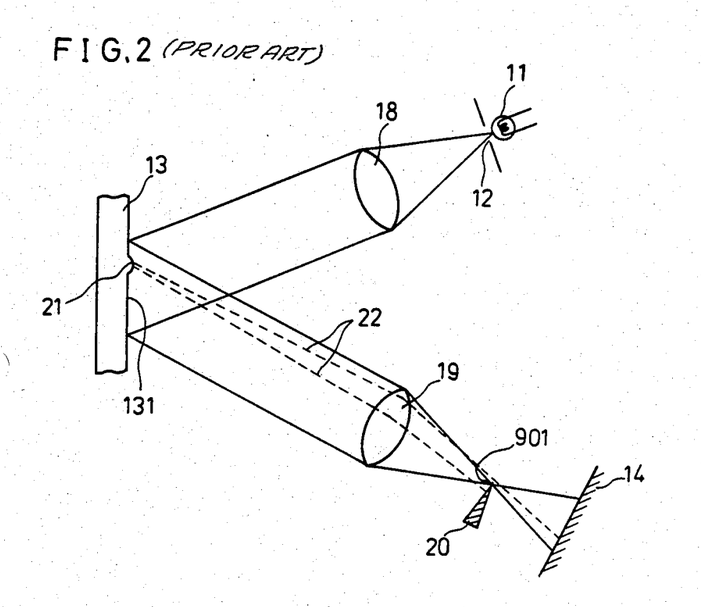
FIG. 2 is a schematical sectional elevation view showing the principle of another conventional surface examining method utilizing a known schlieren apparatus.

Another conventional method for detecting surface defects has been proposed to use schlieren apparatus as shown in FIG. 2, wherein a light from a small light source 11 issued through a pin-hole 12 is converged to substantially parallel rays by a condenser lens 18 and projected onto the examined surface 131 of the substrate 13. Then, light reflected by the substrate surface 131 is converged by a convex lens 19 thereby forming a focussed point 901. A knife edge 20 is provided in a manner that the focussed point just comes on the knife edge so that the rays are shadowed by the knife edge 20 and not to reach on the screen 14, thereby there is no light image formed on the screen 14. When the examined surface 131 has a concave or convex defect, the rays reflected at the defect are not converged to the focussed point 901 but form a beam with a considerable diameter around the focussed point 901, thereby passing over the knife edge 20 and projecting a pattern on the screen 14. Therefore, the convex or concave defect is detected by the forming of a pattern image on the screen. This method has a problem that among the rays scattered by the defect, only a half portion thereof is used as defect information, since half the rays reflected by the defect would be stopped by the knife edge. Therefore, when the rays reflected by the defect are bend downwards in FIG. 2, the rays only impinge on the knife edge, and no detection is made. Furthermore, the apparatus has the problem of requiring a high precision knife edge and frequent adjustment of the focussed point to be on the knife edge 20, and a considerably large size dark room.

Since the above-mentioned conventional examining methods have various problem and are not practical in an actual mass-production factory, the necessary examination has been made by means of the bare-eye observation by skilled workers, and the examination has not been efficient nor reliable. In order to raise the quality of the inspection, the examination has been a sampling test combined with thermal treatment or etching for growing the crystal imperfection for easier detection thereof.

SUMMARY OF THE INVENTION

Accordingly, the present invention purports to provide a method and apparatus capable of detecting very shallow and gentle recesses on a mirror-polished surface on a substrate and observing the detected pattern of the whole area of the surface at one sight by utilizing generally the above-mentioned principle of FIG. 1 but by an improved method and apparatus enabling pratical use thereof.

The present method and apparatus can detect very minute defects on a mirror-polished substrate with a non-contact detection method, and therefore is very useful in the detection of hitherto overlooked defects on the surface of wafers for LSI.

The present invention can provide a method and apparatus for quickly and easily detecting defects without special skill, or by using an automated system.

The method of examining a surface in accordance with the present invention generally relates to the steps of:

shining aligned rays generated from a substantially point light source, making the aligned rays impinge on a surface to be examined, and reflect therefrom, converging the rays reflected from the surface and projecting them onto an image receiving means to form a defocussed image with respect to the surface to be examined, and obtaining a shading pattern in the image, which pattern corresponds to an unevenness on the surface to be examined.

On the other hand, and apparatus for examining a surface in accordance with the present invention may comprise:

a light source for emitting aligned rays which are generated from a substantially point light source, an image-receiving means, a first optical means for converging the aligned rays and making them impinge as evenly distributed rays on a surface to be examined, a second optical means for converging reflected rays and projecting the converged reflected rays to the image-receiving means, the second optical means projecting an image to the image-receiving means as a defocussed image with respect to the surface to be examined.

BRIEF EXPLANATION OF THE DRAWINGS

FIG. 3($a$) is a sectional elevation view of an example of surface examining apparatus embodying the present invention.

FIG. 3($b$) is a diagram showing light intensities at various part of the apparatus of FIG. 3($a$).

FIG. 3($c$) is a sectional elevation view of the example of FIG. 3($a$) for illustration of its operation.

FIG. 4($a$) and FIG. 4($b$) are diagrams for illustrating the principle of the present invention.

FIG. 10($a$), FIG. 10($b$), FIG. 10($c$) and FIG. 10($d$) are sketches of photographs showing defects taken by the apparatus of FIG. 9 and diagrams showing profile of the defects.

FIG. 10($e$) is a diagram showing profiles of the parts $e_1$ and $e_2$ of FIG. 10($d$) drawn by an automatic recorder.

DESCRIPTION OF THE PREFERRED EMBODIMENTS

The inventor confirmed through experiment that in the method of mysterious mirror type surface examination wherein parallel or aligned light is projected onto a mirror-polished surface to be examined and the reflected light is projected onto a light receiving screen to form a light image, a considerably clear pattern corresponding to surface defects are obtainable using a small apparatus when a light-converging optical means such as convex lens or concave mirror is also inserted in the light path between the surface to be examined and the light receiving screen. The present apparatus is small in size, clear in image to be examined and high in sensitivity. In the present invention, a parallel light beam or converging or dispersing but aligned light beam is projected on the surface to be examined, and the reflected light is projected on the light receiving screen or image-receiving means, such as for example a white plain screen, frost glass plate of a viewer, light receiving part (objective lens) of a television camera, or an optical pattern reader, in a manner that on the light receiving screen a light shading pattern is projected as a defocussed light image of the surface.

Figure 3A:
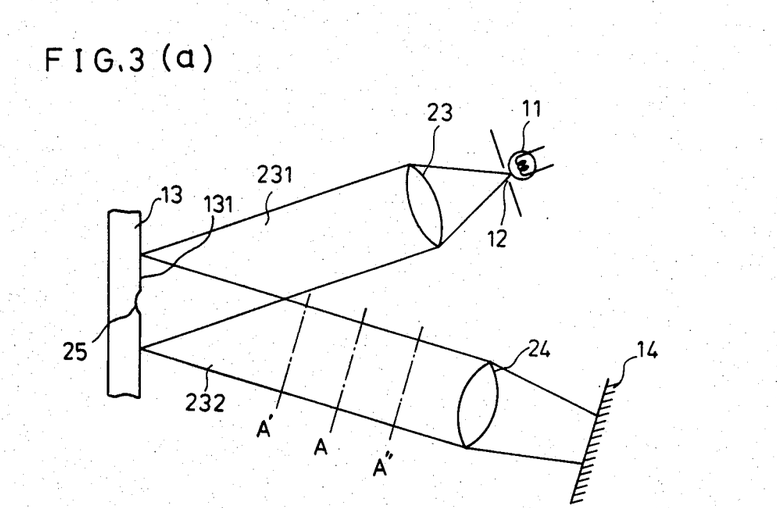
Figure 3B:
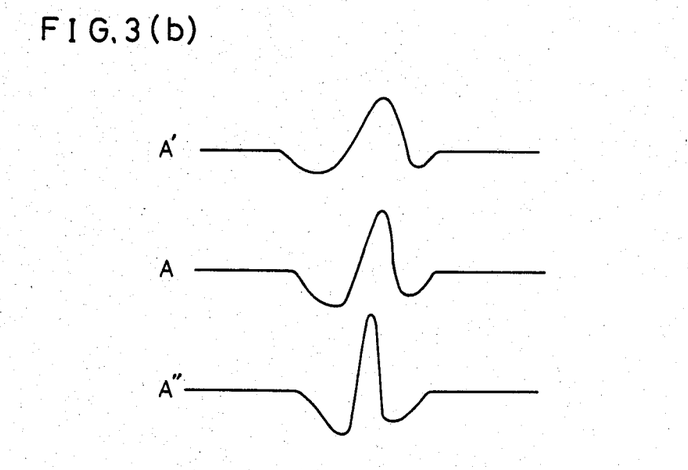

FIG. 3($a$) shows a fundamental embodiment of an exemplary surface examining apparatus in accordance with the present invention, wherein light from a known small light source 11 is emitted through a pin hole 12 through convergence lens 23 of a first optical means to produce substantially parallel rays 231. The parallel rays are then projected on a mirror polished surface 131 of a semiconductor substrate 13 to be examined, which substrate may be starting material of, for example, an LSI or a mirror for a laser. The projected rays 231 are reflected by the surface 131, and the reflected rays 232 are then gently converged by a second convergence lens 24, and the converged rays are projected on a screen 14. The important feature of the method and apparatus of the present invention is that the lens 24 does not focus an image of the reflected rays on the screen. Instead, the reflected rays 232 are projected on the screen 14 as a defocussed image. That is, the focal length of the second convergence lens 24 is selected, for example, shorter than that to focus a real image of the surface 131 on the screen 14. If, for example, the focal length of the projection lens 24 is selected such that an object at position A is projected on the screen as a focussed real image, then the state of rays at the position A is projected on the screen 14. Then when the surface of the substrate 13 is an ideal mirror face 131, the parallel rays, which originated from rays emitted from the point source 11 and converged by the convergence lens 23 and reflected by the mirror face 131, are still parallel rays at the position A, and therefore their distribution at plane A is even. Accordingly, the rays projected on the screen 14 form only an even-brightness image of the shape of the mirror face 131, and no particular pattern is represented thereon. Next, when the substrate 13 has a surface unevenness 25, the unevenness serves as a small concave mirror or convex mirror and makes the reflected rays partially converge or diverge from the ideal parallel rays. Therefore, for example, at the position A, the distribution of rays is made uneven due to the partial convergence or divergence. In FIG. 3(b) curves A, A' and A" show profiles of ray distributions at the positions A, A' and A". As shown in FIG. 3(b), the peak of the profile of the ray distribution is higher as the distance from the surface 131 to the position A, A' or A" becomes farer. The profile of the ray distribution is projected on the screen 14 by the projection lens 24. And by adjusting the position of the lens 24 on its axis, it is possible to find the clearest pattern to be projected on the screen 14. The distance between the surface 131 to be examined and the position A influences resolution of the detection. That is, the point A should be selected as far away from the surface 131 as possible in order to obtain a high resolution.

Figure 3C:
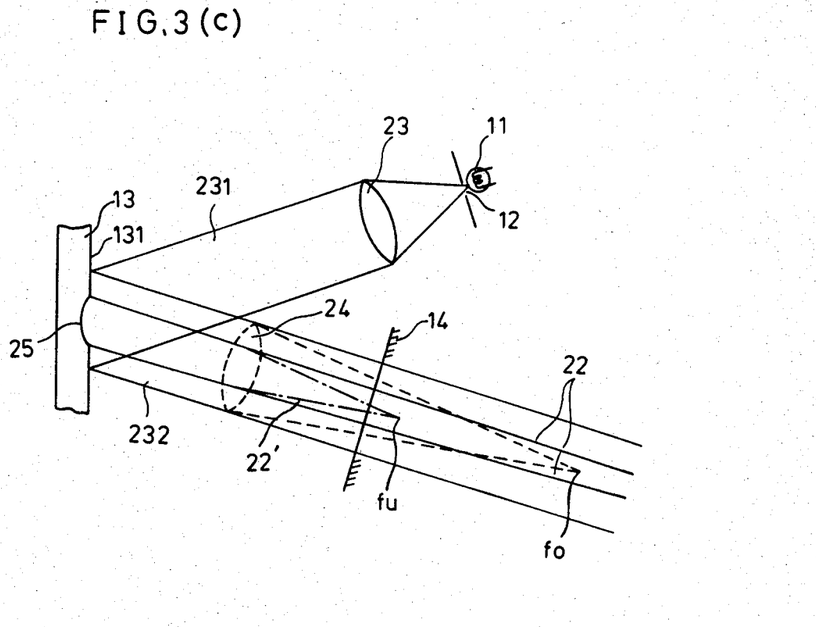

Other elucidation of an example of the present invention is given referring to FIG. 3(c). Rays are emitted from a point source through a pin hole 12 and convergence lens to form parallel rays and impinge on a mirror-polished surface 131 of the substrate 13. The rays 232 reflected by the surface 131 are projected onto the screen 14. Now, it is provided that the surface 131 has a shallow concave part 25, such that having curvature of radius of 50 m and its depth is only 1 μm or less. When there is no convex lens 24 provided between the surface 131 and the screen 14, and the screen 14 is disposed at a distance of 1-2 m from the surface 131, no noticeable pattern is formed in the projected image on the screen 14. This is because the rays converged by the concave part 25 of the surface 131 are not well converged at the position of the screen 14 since the curvature of radius is too long. Therefore, if the screen is disposed at a position of far away by, for example 25 m from the surface 131, then a clear pattern is formed in the projected image. When a convex lens 24 is put in the light path between the surface 131 and the screen 14 disposed at a reasonable distance from the surface, then the rays reflected by the concave part 25 are further converged by the convex lens 24 thereby forming focussed point at the point fu, and the parallel rays 232 forming focussed point at the point fo. Therefore, by disposing a screen at a position around the point fu, a clear pattern based on the concave defect is observable. Therefore, by providing the convex lens 24, the distance to the screen, on which a clear pattern based on the surface unevenness, can be considerably shortened, thereby enabling construction of the whole apparatus around the size of about 1 m. Even when the defect is a convex one, the defect part partly disturbs parallelness of the reflected rays, and also forms unevenness the projected image on the screen.

In the embodiment, the position A, which is the position of a hypothetical object whose clear real image is to be projected on the screen 14, is between the surface 13 to be examined and the screen 14, but instead the position A may be between the point light source 11 and the surface 13 to be examined.

In the apparatus of the present invention, the rays to impinge on the surface 131 to be examined are not limited to parallel rays, but may be convergent rays or divergent rays whenever the rays are originated from parallel rays or a point light source. Therefore, such rays, parallel rays, convergent rays and divergent rays, which are originated from a point light source or parallel rays are defined as aligned rays.

The apparatus of the present invention has an advantage of a high resolution due to the convergence lens or convergence optical means disposed in the light path between the surface examined and the ray-receiving screen. This is elucidated referring to FIG. 4(a) and FIG. 4(b), which are corresponding diagrams of a case with the convergence optical means and a case excluding the convergence optical means, respectively.

Figures 4A, 4B:
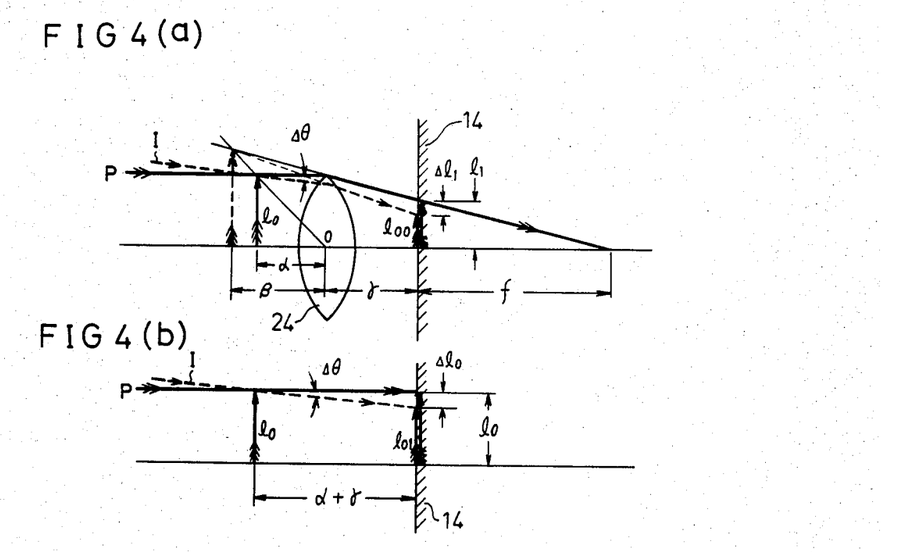

FIG. 4(a) corresponds to the case of FIG. 3(a), and an object $l_0$ on the left side from the lens is at the position A in FIG. 3(a), and the lens 24 and screen 14 corresponds to those in FIG. 3(a). The object $l_0$ and projected image $l_{00}$ are disposed at the positions of distances $\alpha$ and $\gamma$ from the principal face of the lens 24 of the focal length f. Since the lens 24 is provided, the oblique rays I (having angle $\theta$ against the lens axis) reflected by the uneven part of the surface 131 to be examined are bent downwards by the lens 24 and from the image $l_{00}$ on the screen 14. Incidentally, a virtual image corresponding to the projected image $l_{00}$ is at the position of the distance $\beta$. The projected image $l_{00}$, which is formed by the oblique rays I from the uneven part, is projected on the screen 14 at the height of $[l_1 - \Delta l_1]$ which is lower by a difference $\Delta l_1$ from the height of $l_1$, which is for the case of theoretically parallel rays P.

On the other hand, when the lens 24 is removed, the rays are as shown in FIG. 4(b), wherein dotted lines show oblique rays I reflected by the uneven part of the surface 131 to be examined, and solid lines show the theoretically parallel rays P from the theoretically accurate plane of the surface 131. Thus in this "no-lens" case, the projected image $l_{01}$ by the oblique rays I is lower by $\Delta l_0$ than the height of the image $l_0$ formed by the parallel rays P. Now, when the resolution power of the surface examination is defined as "a rate of displacement of the height of the projected image against the height of projected image", then the resolution powers of the cases of FIG. 4(a) and FIG. 4(b) are given by $\Delta l_1/l_1$ and $\Delta l_0/l_0$, respectively. Therefore, as a result of a calculation the ratio between the resolution powers of FIG. 4(a) and FIG. 4(b) are given as follows:

$$\frac{\Delta l_1/l_1}{\Delta l_0/l_0} = 1 + \left| \frac{\gamma^2}{(\alpha + \gamma)(f - \gamma)} \right| > 1.$$

In the equation, the absolute value mark is provided for compatibility both for a convergence lens and a divergence lens as the projection lens 24. As has been elucidated above, the apparatus in accordance with the present invention has a feature that the amplification factor is always larger than 1 by providing the projection lens 24 before the screen or the rays receiving means. That is, resolution power is increased by use of the projection lens 24. And, such a high amplification factor of 3-4 is easily obtainable by the apparatus of the present invention.

Figure 5:
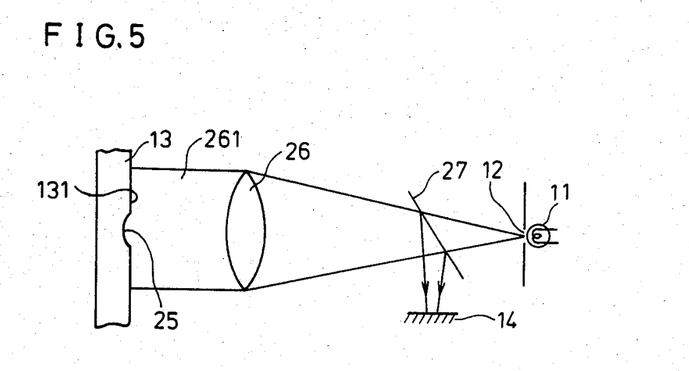
FIG. 5 is a sectional elevation view of another example of surface examining apparatus embodying the present invention.

For the apparatus in accordance with the present invention it is not necessary to use two lenses 23, 24 as shown in FIG. 3(a), but a use of single lens may be possible by using a half-mirror as shown in FIG. 5.

In the embodiment of FIG. 5, rays from a point light source 11 are emitted through a pin hole 12, past the half mirror 27, and converged by a convex lens 26 to form substantially parallel rays 261. The rays 261 are impinged on the surface 131 of the substrate 13 and reflected on the substantially same light path to half mirror 27, whereby the reflected light is reflected to a screen 14. That is, the convergence lens 26 functions twice, first to form parallel rays 261, and second to enable shortening of the distance from the surface 131 to the screen 14. This apparatus has an advantage of small size and low cost by utilizing the same lens for two purposes.

Figure 6:
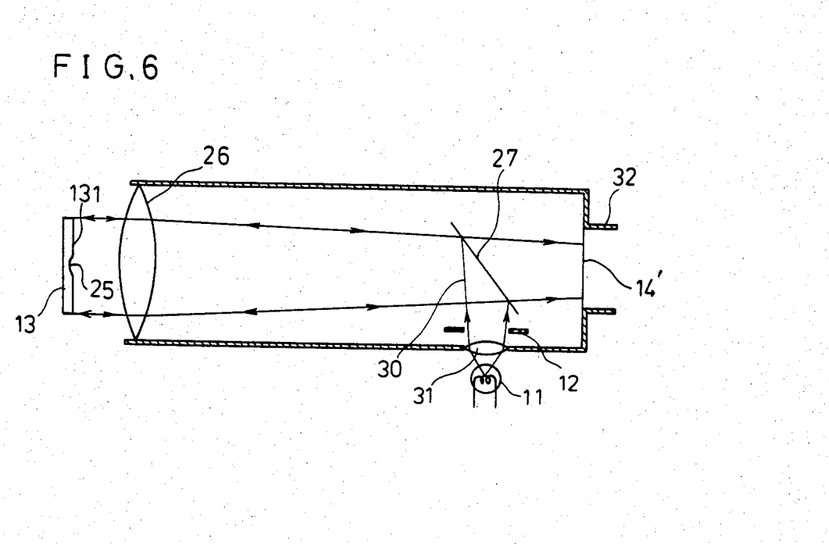
FIG. 6 is a sectional elevation view of still another example of surface examining apparatus embodying the present invention.

FIG. 6 shows a second embodiment. Rays emitted from a point light source 11 are converged by a convergence lens 31 (which is not necessarily needed but is advantageous for increasing brightness) to form aligned rays (which can be made parallel rays when converged by a lens), and reflected by a half mirror 27 towards the substrate surface 131, and through a convex lens 26 impinges on the substrate surface 131. Rays reflected from the substrate surface 131 passe through the convex lens 26 and through the half mirror 27 and are projected on a frost glass screen 14'. By compressing the size of the projected image to ⅓ of the surface 131 to be examined, brightness of the projected image can be made about 9 times as high as that of the embodiment of FIG. 3(a). Therefore the image can be observed in an ordinary room. In order to prevent incidence of ambient light to the observing side (outside) face of the screen 14', it is preferable to provide hood 32. In order to obtain higher resolution, the rays from the point light source 11 may be further delimited by a pin hole aperture of 1 mm or less diameter.

Figure 7:
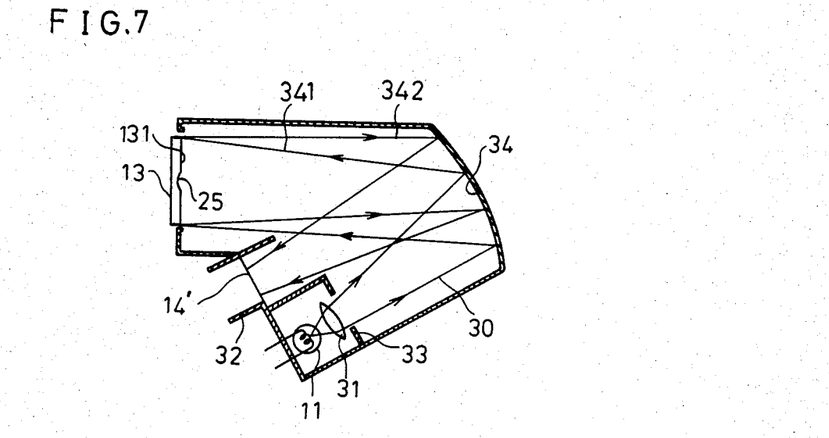
FIG. 7 is a sectional elevation view of still another example of surface examining apparatus embodying the present invention.

FIG. 7 shows another example, wherein rays emitted from a point light source 11 are converged by a convergence lens 31 to form aligned rays 30. In this embodiment, a concave mirror 34 is used as a convergence means. The aligned rays 30 are converged by the concave mirror 34 to form substantially parallel rays 341 which impinge the surface 131. Then reflected rays 342 are again reflected by the concave mirror 34 and are projected to a frost glass screen 14' in a hood 32. By means of the use of the concave mirror as convergence means for two directions of rays, the size of the apparatus can be further halved from that of FIG. 6, and furthermore, brightness is 4-times increased by omission of the half mirror. In case a still camera or TV camera is used to pick up the projected image, with use of such a small point light source of only 0.1 W the surface 131 can be examined on a clear image.

Figure 8:
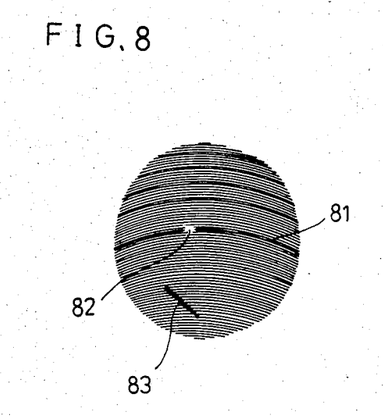
FIG. 8 is a sketch of a photography obtained by an apparatus of FIG. 5.

FIG. 8 is a sketch drawn from a photograph taken by the apparatus of the configuration of FIG. 5, wherein
focal length of the convex lens 26 . . . 1.0 m
point light source 11 . . . 3 W lamp
screen 14 . . . vidicon tube focussed at a position of 35 cm before its objective lens.
substrate 13 . . . 3 inch silicon semiconductor wafer
distance from the light source 11 to the surface 131 . . . 1.3 m
distance from the surface 131 to the screen 14 . . . about 1.3 m.

As shown in FIG. 8, a number of arch stripes are observed on the image.

By a mechanical examination using contact pin (Talystep method), the following are revealed:
Stripes 81 correspond to lap marks of 0.2 to 0.3 μm depth on the substrate surface.
White spot 82 corresponds to a 0.3-0.5 μm depth recess of about 2 mm diameter on the substrate.
Black line 83 corresponds to 20 mm length scratch on the substrate.

When photographing by using the apparatus, the frost glass as the screen 14 or 14' is removed, and the camera lens is adjusted as if to photograph an object at 30 cm distance, and exposure time is 10 seconds using an ASA 100 film at lens stop value of F=2.

The above result is very advantageous in comparison with the simple mysterious mirror method shown in FIG. 1 wherein, the distance from the surface examined and the screen should be 5-6 m or more, and a high power light source as well as highly sensitive screen are necessary, with a large dark room also necessary.

The lens may be a composite lens comprising several component lenses.

In case the projecting lens of FIG. 5 between the surface 131 to be examined and the screen 14 comprises several component lenses, the lens is preferably designed such that its objective position, the image of which is to be focussed on the screen, is between a convex component lens which is closest to the screen and the surface to be examined. However, apart from the above configuration, the objective position may be disposed between the light source 11 and the sourface 131.

Figure 9:
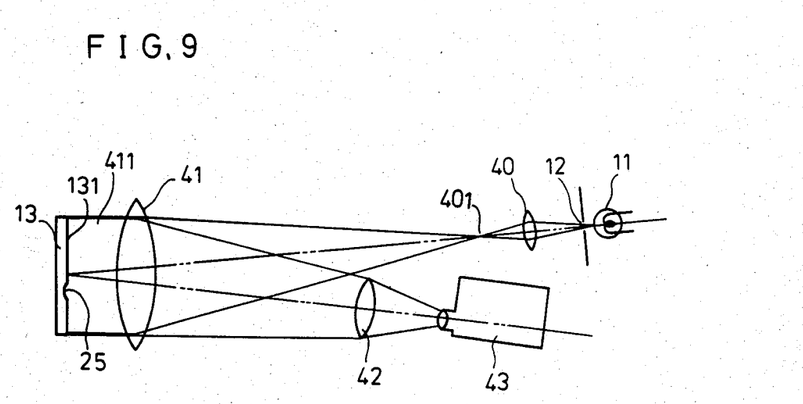
FIG. 9 is a sectional elevation view of still another example of surface examining apparatus embodying the present invention.

FIG. 9 shows an example system where a monitoring TV camera 43 is used with the apparatus in accordance with the present invention. Therein, rays are emitted from a point light source 11 through pin hole 12 about 1 mm diameter in front thereof, and the rays diverging therefrom are then converged by a convex lens of 30 mm of diameter and 100 mm focal length to form a focussed point 401. The rays further diverge from the focussed point 401 and pass a large convex lens 41 of 125 mm diameter and 1000 mm focal length, thereby being converted into parallel rays 411. That is, the lens 41 is so disposed that its one focus is around the focussed point 401. A substrate wafer surface 131 thereof to be examined is disposed on a wafer holder about 50 mm distance from the large convex lens 41. Reflected rays are converged again by the large diameter convex lens 41 and further converged by a small convex lens 42 of 50 mm diameter and 500 mm focal length, and the rays are projected to the objective lens of the monitor camera 43 in a manner that converged rays cover the whole incident area of the objective lens and have an angle of the maximum visual angle of the objective lens. Accordingly, to the pickup device of the camera, the image based on the unevenness of the surface is projected at the full size thereof. By adjusting the axial positions of the lenses 40, 41 and 42, the incident angle and diameter of the incident rays to the objective lens of the monitor TV camera 43 can be adjusted, so that the size of the image is adjustable for easy examination.

As a modified example, the rays may be introduced directly onto the pickup device of the monitoring TV camera without passing the objective lens thereof.

In the above-mentioned apparatus, the alignment of the rays become more accurate by use of the first lens 40 thereby to make a focussed point as a rays source. By use of the large convex lens 41, the distance between the light source 11 and the surface 131 to be examined, as well as the distance between the surface 131 to the screen to receive images, can be shortened.

If the system were constructed in a manner that rays from the point source directly impinge the surface 131 without use of the large lens 41, then the substrate must be far distant from the large lens 41 for convergence of the reflected rays. In order to minimize parallax, the distance should be farer, and this further requires larger diameter of the large lens 41, since reflected rays are divergent.

In the above-mentioned embodiment of FIG. 9, the whole apparatus is contained in a 300 mm×300 mm×1300 mm box, and an ordinary monitor TV camera with vidicon pickup tube is installed thereon with its objective lens adjusted at a closest distance position (450 mm). By this apparatus, the objective position, of which real image is focussed in the camera, is adjusted at 500 mm to 700 mm from the surface 131 towards the lens 42, and thereby patterns corresponding to unevenness of the surface are observed through the TV camera.

FIG. 10(a), FIG. 10(b), FIG. 10(c) and FIG. 10(d) show shading patterns of various unevenness of the surface, wherein:

stripes 81 . . . corresponds to Lap marks (uneven parts produced when lapping the substrate surface), spot 82 . . . corresponds to a Dimple which is produced by an undesirable pinching of a dust particle between the substrate 13 and a substrate holder when lapping the substrate surface 131, line 83 . . . corresponds to a scratch, smears 85 . . . corresponds to back side damage (the surface unevenness induced by mechanical shock on the back side of the substrate by, for example, sand-blast, etc.).

Figure 10A:
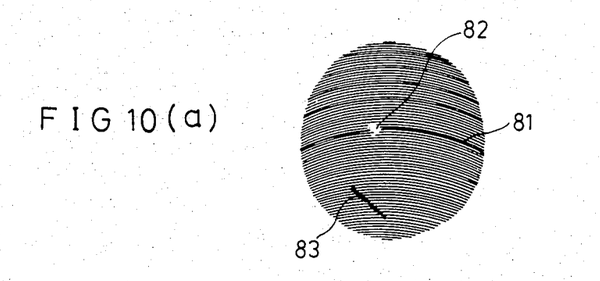
Figure 10B:
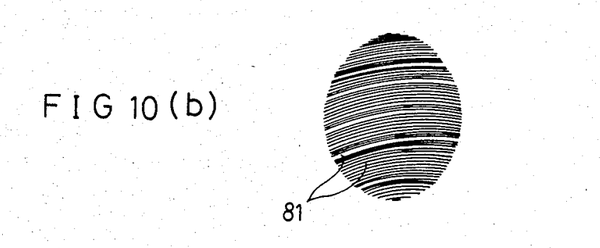
Figure 10C:
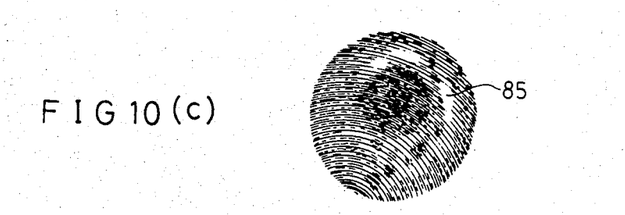
Figure 10D:
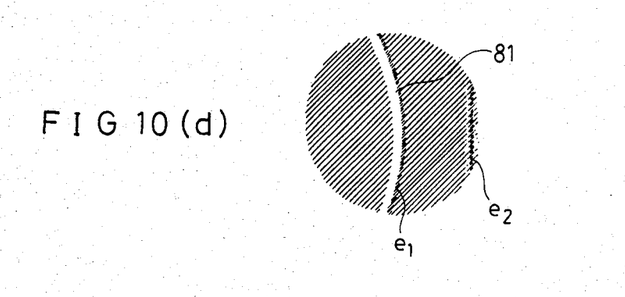
Figure 10E:
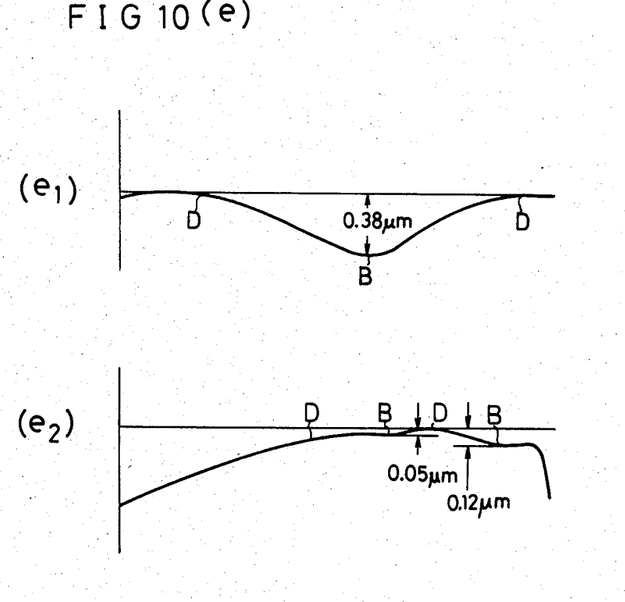

FIG. 10(e) is a diagram showing profiles of the parts $e_1$ and $e_2$ of FIG. 10(d) drawn by an automatic recorder when the surfaces corresponding to the Lap marks are examined by mechanical surface roughness meter. In FIG. 10(e), the marks D and B designate dark part and bright part of the image, respectively. As shown on the diagram, such a shallow unevennesses as 0.05 μm are detected. Through such comparison tests, it is confirmed that the apparatus of the present invention can detect such shallow and gentle unevenness of the curvature radius of 1 m to 100 m or more. Also, a scratch, which has the curvature radius of under 1 m can be detected.

The present invention is of course applicable for the surface examination of various items, not only for semiconductor wafer, but also for light recording disk, laser mirror, etc.

What is claimed is:

1. A surface examining apparatus, comprising:
   a substantially point light source for emitting light rays,
   an image-receiving means for receiving images,
   first optical means for converging said rays and for making them impinge as evenly distributed rays on a surface to be examined, and
   second optical means for converging rays reflected from said surface and for projecting said converged reflected rays substantially undiminished to said image-receiving means, said second optical means projecting an image to said image-receiving means constituting a defocussed image of said surface to be examined.

2. A surface examining apparatus in accordance with claim 1, wherein said second optical means comprises a convex lens.

3. A surface examining apparatus in accordance with claim 1, wherein said first optical means and said second optical means commonly comprise a single convex lens.

4. A surface examining apparatus in accordance with claim 1, wherein said first optical means and said second optical means comprises at least in one part thereof a half mirror.

5. A surface examining apparatus in accordance with claim 1, wherein said first optical means and said second optical means comprises at least in one part thereof a concave mirror.

6. A surface examining apparatus in accordance with claim 1, wherein, said image-receiving means is a camera.

7. A surface examining apparatus in accordance with claim 1, wherein, said first optical means comprises a ray condenser lens and a large convergence lens and said second optical means comprises said large convergence lens and another convergence lens.

8. A surface examining apparatus, comprising:
   a substantially point light source for emitting light rays,
   an image-receiving means for receiving images,
   first optical means for converging said rays and for making them impinge as evenly distributed rays on a surface of a semiconductor wafer, and
   second optical means for converging rays reflected from said surface and for projecting said converged reflected rays substantially undiminished to said image-receiving means, said second optical means projecting an image to said image-receiving means constituting a defocussed image of said surface of said semiconductor wafer.

9. A surface examining apparatus in accordance with claim 8, wherein, said second optical means comprises a convex lens.

10. A surface examining apparatus in accordance with claim 8, wherein said first optical means and said second optical means commonly comprise a single convex lens.

11. A surface examining apparatus in accordance with claim 8, wherein said first optical means and said second optical means comprises at least in one part thereof a half mirror.

12. A surface examining apparatus in accordance with claim 8, wherein said first optical means and said second optical means comprises at least in one part thereof a concave mirror.

13. A surface examining apparatus in accordance with claim 8, wherein said image-receiving means is a camera.

14. A surface examining apparatus in accordance with claim 8, wherein said first optical means comprises a ray condensor lens and a large convergence lens and said second optical means comprises said large convergence lens and another convergence lens.

15. A method for examining a surface, comprising the steps of:
   shining light rays from a substantially point light source, making said rays impinge on a surface to be examined, and reflect therefrom, converging the rays reflected from said surface and projecting them substantially undiminished onto an image-receiving means to form a defocussed image with respect to said surface to be examined, and obtaining a shading pattern in said defocussed image which corresponds to an unevenness on said surface to be examined.

16. A method for examining a surface in accordance with claim 15, wherein said impinging of said light rays on said surface is made by means of a first convex lens, and said converging and projecting of said reflected rays is made by means of a second convex lens.

17. A method for examining a surface in accordance with claim 15, wherein said impinging of said light rays on said surface and said converging and projecting of said reflected rays are made by means of a common convex lens.

18. A method for examining a surface in accordance with claim 15, wherein said impinging is made via a half mirror.

19. A method for examining a surface in accordance with claim 15, wherein said projecting of said reflected rays is made to a camera disposed as said image receiving means.

20. A method for examining a surface in accordance with claim 15, wherein said shining of said light rays is made by means of a condenser lens, said impinging of said aligned rays on said surface to be examined is made by means of a large diameter convex lens, said projecting of said image is made by means of said large diameter lens and an additional convergence lens.

21. A method for examining a surface, comprising the steps of:

shining light rays from a substantially point light source;

making said rays impinge on a surface of a semiconductor wafer, and reflect therefrom, converging the rays reflected from said surface and projecting them substantially undiminished onto an image-receiving means to form a defocussed image with respect to said surface of a semiconductor wafer, and obtaining a shading pattern in said defocussed image which corresponds to an unevenness on said surface of said semiconductor wafer.

22. A method for examining a surface in accordance with claim 21, wherein said impinging of said light rays on said surface is made by means of a first convex lens, and said converging and projecting of said reflected rays is made by means of a second convex lens.

23. A method for examining a surface in accordance with claim 21, wherein said impinging of said light rays on said surface and said converging and projecting of said reflected rays are made by means of a common convex lens.

24. A method for examining a surface in accordance with claim 21, wherein said impinging is made via a half mirror.

25. A method for examining a surface in accordance with claim 21, wherein said projecting of said reflected rays is made to a camera disposed as said image receiving means.

26. A method for examining a surface in accordance with claim 21, wherein said shining of said light rays is made by means of a condenser lens, said impinging of said light rays on said surface of said semiconductor wafer is made by means of a large diameter convex lens, said projecting of said image is made by means of said large diameter lens and an additional convergence lens.

* * * * *